United States Patent [19]

Olson

[11] Patent Number: 4,504,200
[45] Date of Patent: Mar. 12, 1985

[54] MINIATURE INFUSION PUMP

[75] Inventor: Raymond G. Olson, Niles, Ill.

[73] Assignee: Baxter Travenol Laboratories, Inc., Deerfield, Ill.

[21] Appl. No.: 104,407

[22] Filed: Dec. 17, 1979

[51] Int. Cl.³ .................... F04B 43/12; F04B 45/08
[52] U.S. Cl. ...................................... 417/476; 418/45
[58] Field of Search ................... 417/476, 477; 418/45

[56] References Cited

U.S. PATENT DOCUMENTS

| | | | |
|---|---|---|---|
| 2,679,807 | 6/1954 | Bruckmann | 417/476 X |
| 2,818,815 | 1/1958 | Corneil | 417/475 |
| 3,384,080 | 5/1968 | Muller | 417/477 |
| 3,908,657 | 9/1975 | Kowarski | 128/278 |
| 3,927,955 | 12/1975 | Spinosa et al. | 417/477 |
| 4,006,743 | 2/1977 | Kowarski | 128/214 R |
| 4,008,717 | 2/1977 | Kowarski | 128/214 R |

Primary Examiner—Richard E. Gluck
Attorney, Agent, or Firm—Paul C. Flattery; Garrettson Ellis; Bradford R. L. Price

[57] ABSTRACT

A pressure pump for fluids in flexible tubing, which comprises a pressure member of generally circular periphery adapted for orbital motion about an axis of rotation. A sleeve member is positioned about the pressure member and defines channel means for receiving and retaining the flexible tubing in a predetermined position between the pressure member and sleeve member, and surrounding the pressure member. The sleeve member may be divided into a pair of substantially semi-circular jaws attached together at one end in hinged relation, to permit opening and closing of the jaws about the pressure member to facilitate installation of the tubing.

20 Claims, 10 Drawing Figures

FIG. 9
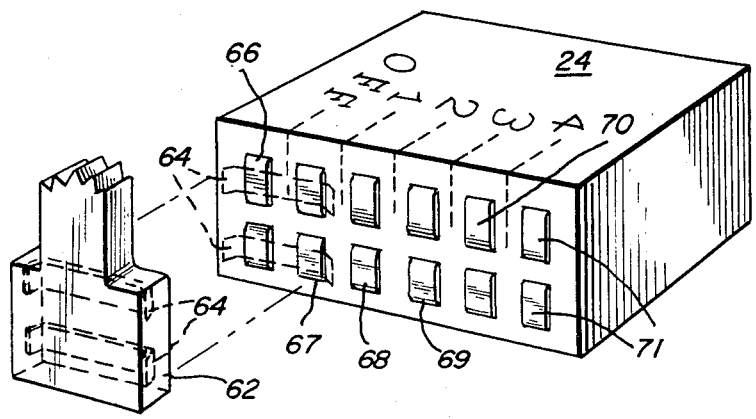
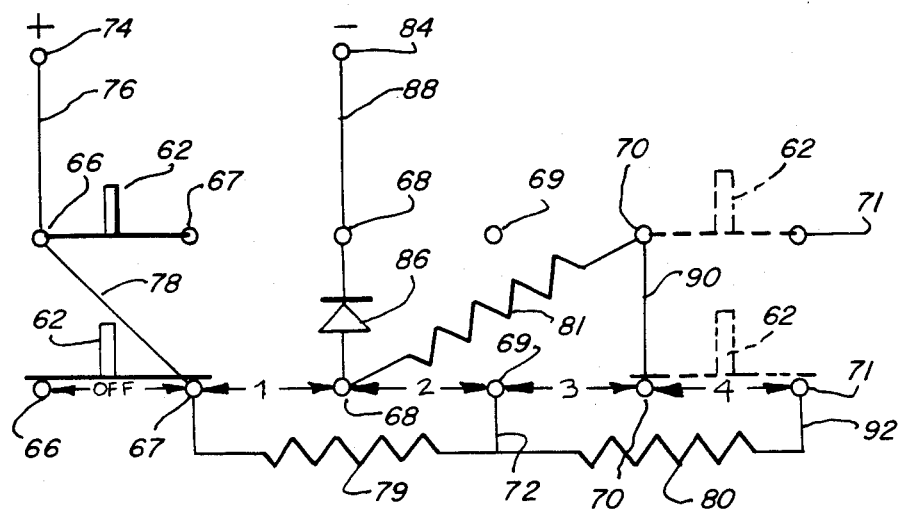
FIG. 10

MINIATURE INFUSION PUMP

BACKGROUND OF THE INVENTION

In U.S. Pat. No. 3,908,657, a small, wearable medical pump for fluids is disclosed. Also, wearable pumps which comprise a pressure member adapted for orbital motion about an axis of rotation to pump liquids through flexible tubing are commercially available, and may be worn for either the withdrawal of blood for medical purposes or for the controlled infusion of critical medications which should be administered in very low but constant concentrations on an all-day basis. Accordingly, the patient is able to engage in his normal activities while wearing such a pump.

Such a pump is manufactured by Cormed, Inc. of Middleport, N.Y. The pressure member adated for orbital motion is surrounded by a rigid sleeve, which defines an annular groove in its end. The tubing for pumping is forced into the end groove for operation of the pump.

This, however, provides a substantial disadvantage in that the tubing is difficult to get into the groove and into engagement with the pump head or pressure member without being pushed in by a pointed instrument of some kind. This, in turn, can damage the tubing if not done carefully.

Also, the above-cited miniature pump defines a single side slot, into which the tubing enters and exits from the rigid sleeve which surrounds the pump head. At those times, when the pump head is positioned against the side slot, it is possible for liquids to flow through the tubing in an uncontrolled manner, since the side slot provides a position for the tubing sections to retreat from the pump head, and thereby not be closed by the head as in the normal mode of operation. Particularly, if by chance the pump head is stopped in a position against the slot, flow can take place in a free and uncontrolled manner through the tubing, which is most undesirable, particularly when a critical dosage medicament is being administered.

In accordance with this invention, an improved orbital motion tubing pump is provided, which is preferably miniaturized for wearing, in which the installed tubing is prevented from free flow within its bore in all positions of the pressure member or pump head. Furthermore, means are provided for more convenient installation of the tubing about the pump head in a manner which can be less damaging to the tubing.

Other advantages are also provided by the improved pump of this invention as described below.

DESCRIPTION OF THE INVENTION

The pump of this invention is a pressure pump for fluids through flexible tubing, which comprises: a pressure member of generally circular periphery adapted for orbital motion about an axis of rotation. A sleeve member is positioned about the pressure member and defining channel means for receiving and retaining flexible tubing in a predetermined position between the pressure member and sleeve member, with the tubing surrounding the pressure member.

In accordance with this invention, the sleeve member is divided into a pair of substantially semi-circular jaws attached together at one end in hinged relation, to permit opening and closing of the jaws about the pressure member, to facilitate installation of the tubing.

Preferably, the jaws define a tubing inlet slot transversely across one side of one of the jaws, and a tubing outlet slot positioned transversely across the opposite side of one of the jaws. The slots are preferably of no more depth than about one half the height of the jaws, the slots being circumferentially spaced from each other about said jaws by at least 30°, and preferably 120° to 180°.

The pressure member and sleeve member may be carried by a housing, with the housing being, in turn, carried by an openable casing, adapted to receive a flexible liquid container having flexible tubing for connection through the pressure pump. The pressure member and jaws may project from the casing toward the exterior.

If desired, a longitudinal slot may be defined in the housing to receive the flexible tubing, with the tubing inlet slot being positioned on the side of the jaws that faces the casing, and an end of the tubing inlet slot being positioned adjacent to the outer end of the longitudinal slot, to permit tubing in the longitudinal groove to pass into the inlet slot.

A transverse slot in the housing may carry stop pin means for engaging and preventing rotation of the pressure member during operation. Means are thus provided for orbital motion of the pressure member, with such orbital motion means rotating inside of the non-rotating pressure member. This, preferably, may be accomplished by carrying the pressure member on a crank member for the orbital motion by rotation of the crank member, with electric motor means being provided for rotating the crank member.

Removable outer cap means may be provided, for positioning about the jaws, in which the outer cap means defines a side wall and slot means in the side wall to permit installation of the cap means after installation of the flexible tubing about the pressure member, with the slot means terminating in a circumferentially enlarged area, which is positioned by the cap means at the circumferentially outer end of the tubing outlet slot.

The electric motor means which rotates the crank member may be controlled by multiple position switch means, and circuitry adapted to provide variable resistance in a manner dependant upon the position of the switch of the multiple position switch means, to provide adjustable motor speed for varying the flow rate of the pump.

In the drawings,

FIG. 9 is an enlarged perspective view of the multiple position switch means utilized in this invention.

FIG. 10 is a schematic circuit diagram showing the circuitry of the multiple position switch means.

Figure 1:
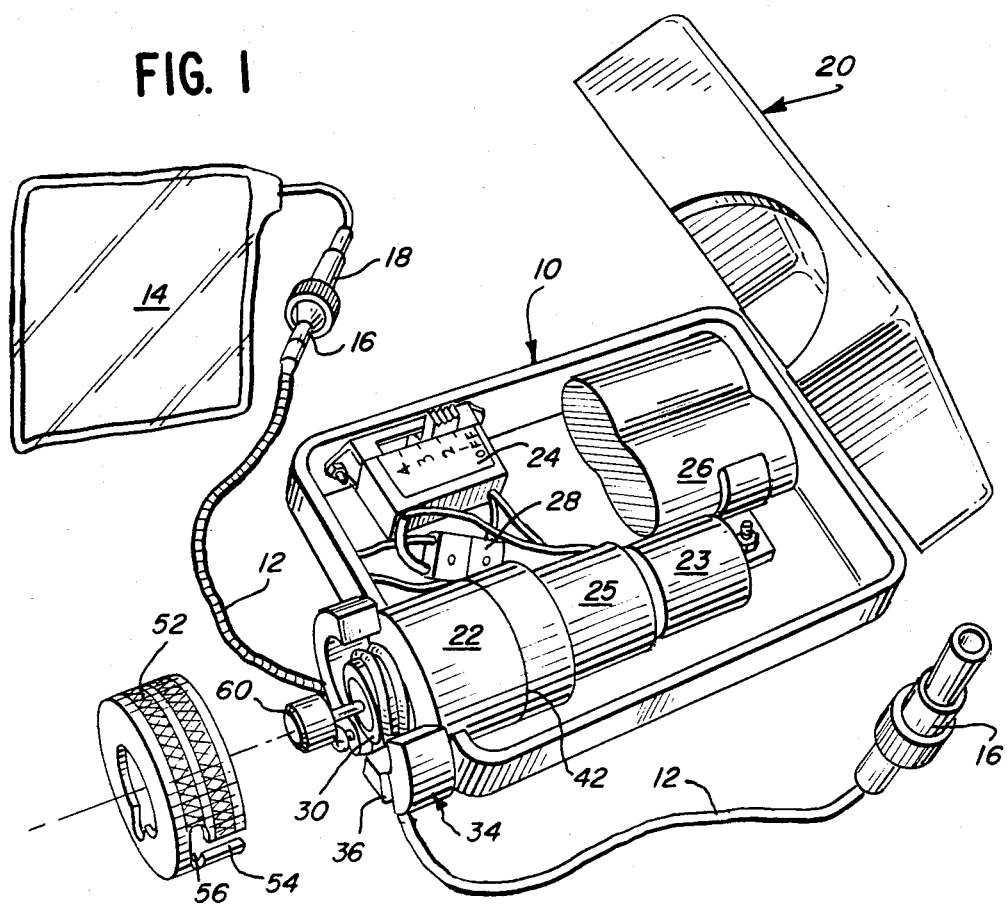
FIG. 1 is a perspective view, with the upper casing half broken away, of the pump of FIG. 1.
Figure 2:
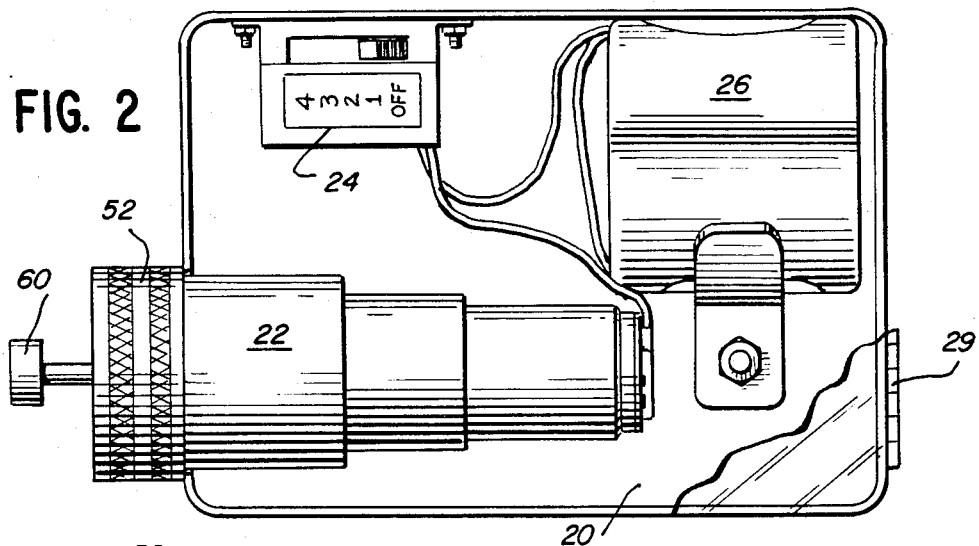
FIG. 2 is a plan view, with portions of the upper casing half broken away, of the pump of FIG. 1.
Figure 3:
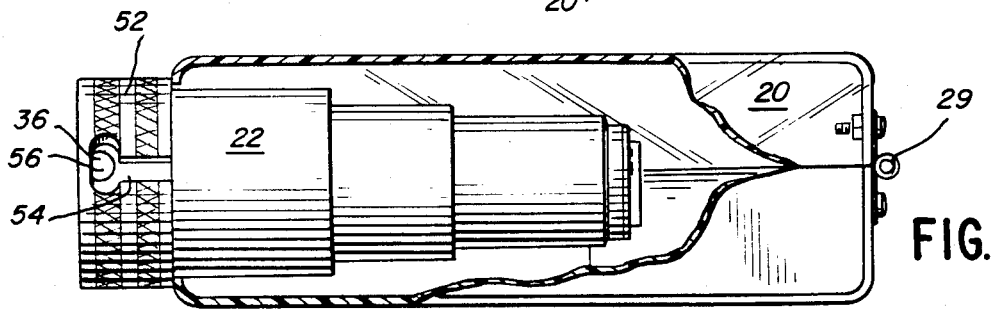
FIG. 3 is an elevational view, with portions broken away, of the pump of FIG. 2.

Referring to the drawings, FIGS. 1 through 3 disclose a pressure pump apparatus 10 for fluids through flexible tubing 12, which tubing is connected to a bag 14 and may constitute a sterile set having conventional luer type connectors 16 at opposite ends thereof, one of which may be connected to a luer adaptor 18 on the bag 14, and the other of which is available for connection to an infusion needle in the vein of a patient. Accordingly, the contents of bag 14 may be connected through tubing 12 to the venous system of the patient.

Bag 14 may be then positioned within openable casing 20, along with the rest of the apparatus of this invention, and held in a pouch on the patient's body while the pump of this invention operates, permitting the patient to go about normal daily activities while the medicament in bag 14 is slowly administered to him throughout the day.

Specifically, the apparatus of this invention may be used for administering controlled, continuous amounts of a chemotherapy agent for cancer patients, or any other critical dose material where a continuous administration over the course of a day is deemed to be advantageous over the intermittent administration of large doses of the medicament.

Positioned within casing 20 is a pressure pump 22, which may be electrically operated through multiple position switch 24, being powered by battery pack 26. Pump 22 includes motor 23, and gear box 25. The circuitry between these elements includes joined connectors 28 to permit removal and replacement of battery pack 26 when it is exhausted.

Casing 20 has hinges 29 as shown, and may be conventionally latched for opening and closing as desired.

Pump 22 defines a pressure member 30, typically of generally circular periphery, and adapted for orbital motion about an axis of rotation 32. The amount of offset of pressure member 30, as shown by line 33 (FIG. 4), is preferably about 1/32 inch in the miniature, wearable version of the pump of this invention.

Sleeve member 34 is positioned about the pressure member 32, and defines outlet and inlet channel means 36, 38 (FIG. 6) on its top and bottom surfaces for receiving and retaining the flexible tubing 12 in a predetermined position, coiled about the pressure member 30 and enclosed within sleeve member 34.

In accordance with this invention, sleeve member 34 may comprise a pair of substantially semi-circular jaws 34a, 34b, each of which are preferably of substantially semi-circular shape, and attached together at one end by a hinge member, shown here to be a bolt 40 penetrating through apertures in each of the jaws 34a, 34b and attached to pump 22. This permits opening and closing of the jaws about the pressure member to facilitate installation of the tubing while the jaws 34a, 34b are opened, and then to permit closing of the jaws about the tubing coiled about pressure member 30.

A portion of jaw 34a defines a bevelled inner edge adjacent slot 38 and extending from slot 38 toward the free end 39 of jaw 34a. The purpose of this is to prevent pinching and damage of the flexible tubing upon closing of the jaws.

Figure 6:
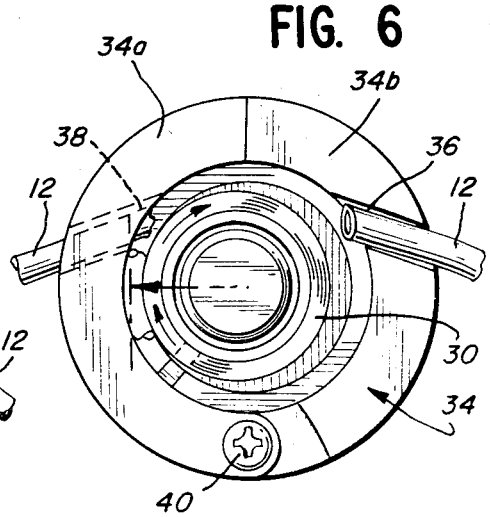
FIG. 6 is a view similar to FIG. 5, showing the sleeve member jaws in closed position and showing the tubing installed therein partly broken away for purposes of clarity.
Figure 7:
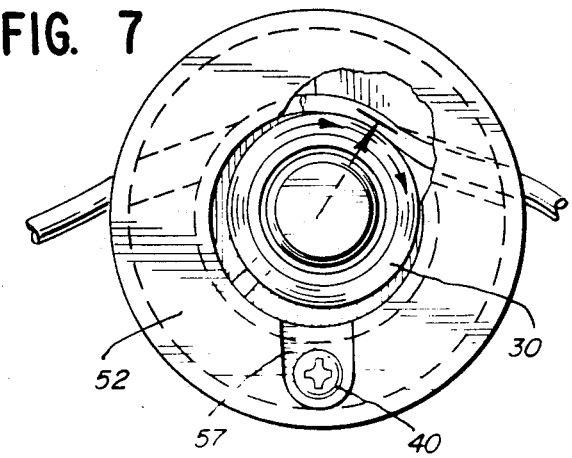
FIG. 7 is a view similar to FIG. 6 but showing the pressure member in different orbital position from that of FIG. 6, and carrying the outer cap.

In this configuration, as shown for example in FIGS. 6 and 7, as sleeve member 30 moves in orbital motion, impelled by motor 23, liquid is forced through tubing 12 in one direction by the orbital action of pressure member 30, pressing tubing against the closed sleeve member 34. The minimum space between closed sleeve member 34 and pressure member 30 is sufficient to compress tubing 12 so that no fluid can flow. Thus, the moving orbital action of pressure member 30 forces fluid through tubing 12 in a manner corresponding to its rate of orbital motion.

Figure 4:
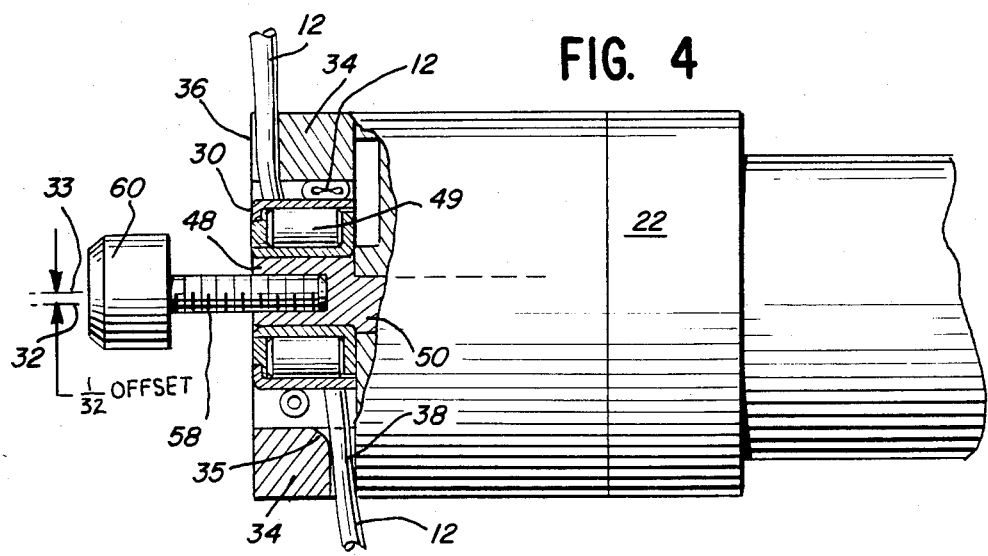
FIG. 4 is an enlarged fragmentary, elevational view, with portions broken away, of the area of the pump head of the pump of FIGS. 1-3.
Figure 5:
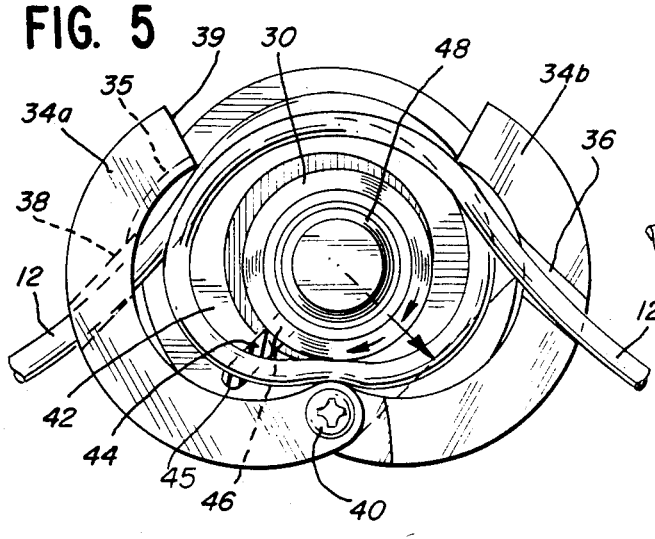
FIG. 5 is an elevational view, taken 90° from the view of FIG. 4, showing the pump head with the sleeve member jaws in open position.

The housing 42 of pump 22 defines a transverse slot 44 which carries stop pin means 45 for engaging pressure member 30 in aperture 46 (FIG. 5) and preventing rotation of the pressure member. Pressure member 30 is shown in FIG. 4 to be carried on a crank member 48 which is eccentrically positioned at the end of drive shaft 50 of electric motor 23 so that it orbits about axis of rotation 32, carrying pressure member with it, but pressure member 30 remains in stationary, non-rotating relation to tubing 12 while crank member 48 rotates within the pressure member 30 so that the pressure member does not abrade against tubing 12 but merely presses against it in an orbital manner.

Pressure member 30 is positioned in rotational relationship about crank member 48 by a roller bearing 49, or other suitable bearing as may be desired to facilitate the stationary orbital motion of pressure member 30 as crank 48 rotates, impelled by drive shaft 50 of the pump 22.

Figure 8:
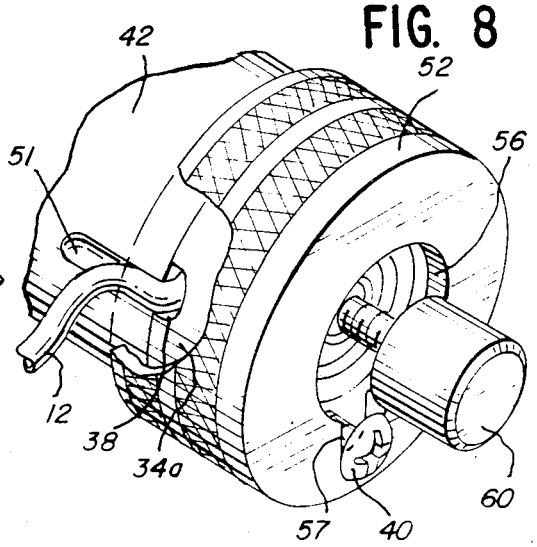
FIG. 8 is a fragmentary, perspective view of the pump head of FIGS. 4-7, carrying the outer cap.

Preferably, slots 36, 38 are of no more than one half the height of jaws 34a, 34b, as shown for example in FIG. 8, with the slots being circumferentially spaced from each other as shown by at least 30° and preferably about 120° to 180° about the circumference of sleeve member 34.

Preferably, longitudinal groove 51 (FIG. 8) is defined in the housing 42 of motor 22 to receive flexible tubing 12, with tubing inlet slot 38 being positioned on the side of one of the jaws 34a that faces casing 42. An end of tubing inlet slot 38 is positioned adjacent the outer end of the longitudinal groove, to permit tubing in the longitudinal groove to pass into the inlet slot. Therefore, as shown in FIG. 8, the tubing 12 can pass under removable outer cap means 52 as shown. Outer cap means 52 is adapted to fit about the closed jaws 34a, 34b to retain them in the closed position, after the tubing 12 has been loaded into the pump, and the pump is ready for operation.

Outer cap means 52 defines a side wall, and slot means 54 in the side wall to permit installation of the cap means after installation of the flexible tubing about the pressure member. Slot means 54 terminates in a circumferentially enlarged area 56 which may be positioned by the cap means at the circumferentially outer end of tubing outlet slot 36 so that cap means 52 may be placed on and removed from the jaws while tubing 12 is engaged with the pump apparatus.

Retention bolt 40 which defines the hinged connection for jaws 34a, 34b, defines a flanged head and a small clearance between the outer surface of the jaw 34a and the head of bolt 40.

Slot 57 of cap 52, extending radially outwardly from an aperture 56 of cap 52, is of a width to permit the head of bolt 40 to pass through slot 57, to install or remove cap 52. When cap 52 is desired to be retained on housing 42, it is rotated so that a portion of its wall passes under the head of bolt 40, for retention thereof.

Armature extension 58, attached to handle means 60, is attached to the drive shaft 50, and permits it to be manually rotated to facilitate the installation of tubing 12 into its operating position between pressure member 30 and sleeve member 34, and to permit manual pumping to eliminate air from tubing 12.

FIG. 9 shows a detailed view of multiple position switch means 24, which serves to adjust the speed of electric motor 22. Sliding switch 62 defines contacts 64 which are capable of providing electrical communication between separate pairs of terminals 66 through 71.

As shown in FIG. 10, the electrical circuit includes positive terminal 74, which communicates with one of terminals 66 through wire 76. Terminal 66 and one of terminals 67 communicate through wire 78. Resistors 79, 80 and 81 communicate with respective terminals 67 through 71 in the pattern shown. Wire 72 forms a junction between resistors 79 and 80.

As shown in the specific embodiment, one each of terminals 66, 67, 69 and 71 are unconnected, but may optionally be present for simplicity of design, if a standard commercial multiple position switch is utilized.

Accordingly, when sliding switch member 62 is positioned between terminals 66 and 67, there is no connection between positive terminal 74 and negative terminal 84. No electrical path exists between the two terminals.

When sliding switch 62 is positioned between terminals 67 and 68, an electrical flow path is formed that does not flow through any of resistors 79-81, permitting operation of the motor at top speed. The electrical flow path passes through lines 76 and 78, and then through diode 86, which is provided to prevent reverse flow of current in the system, so motor 22 does not run backwards. From there, the current passes through line 88 to close the circuit.

When sliding switch 62 is in a position connecting terminals 68 and 69, the current flow is through lines 76 and 78, then passing through resistor 79 and line 72, followed by current passage through switch 62, diode 86, and line 88 to complete the circuit. Accordingly, motor 22 runs more slowly in this mode of operation because of the presence of resistor 79 in the circuit.

When sliding switch 62 is positioned between terminals 69 and 70, the flow path is modified, in that after passing through resistor 79, it passes through line 72, sliding switch 62, line 90, and then through resistor 81, diode 86, and line 88 to complete the circuit. Accordingly, the second resistor 81 being added in series to the circuit provides motor operation of a further reduced defined speed.

Finally, when sliding switch 62, as shown in phantom, is in its fifth position between terminals 70 and 71, current passes through resistor 79, resistor 80, line 92, sliding switch 62, line 90, resistor 81, and then diode 86 and line 88 to complete the circuit. Accordingly, motor 22 runs at its lowest speed, since all three resistors are now in the circuit in series relationship.

The invention of this application accordingly provides an improved wearable system for the administration of critical medicaments and the like over a long term, continuous basis to a patient, in which the flexible tubing installation is easier and more reliable, and other substantial advantages are provided. It may also be used to withdraw blood.

The above has been offered for illustrative purposes only, and is not intended to limit the invention of this application, which is as defined in the claims below.

That which is claimed is:

1. In a pressure pump for pumping fluids through flexible tubing which comprises a pressure member of generally circular periphery, adapted for orbital motion about an axis of rotation, and a sleeve member positioned about the pressure member and defining channel means for receiving and retaining said flexible tubing in a predetermined position between the pressure member and sleeve member, with the tubing surrounding said pressure member, the improvement comprising, in combination:

said sleeve member being divided into a pair of substantially semi-circular jaws attached together at one end in hinged relation, to permit opening and closing of said jaws about said pressure member to facilitate installation of said tubing, said jaws defining opposed axial faces, one of said faces defining a tubing inlet slot extending transversely thereacross and the other of said opposed axial faces defining a tubing outlet slot extending transversely thereacross, said slots being circumferentially spaced from each other about said jaws by at least 30°, said pressure member and sleeve member being carried by a housing, said housing being carried by an openable casing adapted to receive a flexible liquid container having flexible tubing for connection through said pressure pump, the pressure member and jaws projecting from said casing toward the exterior, a longitudinal groove defined in said housing to receive said flexible tubing, said tubing inlet slot being positioned on the side of said jaws that faces said casing, an end of said tubing inlet slot being positioned adjacent to the outer end of said longitudinal groove, to permit tubing in said longitudinal groove to pass into said inlet slot.

2. The pressure pump of claim 1 in which said jaws are retained in removable outer cap means.

3. The pressure pump of claim 2 in which said outer cap means defines a side wall, and slot means in said side wall to permit installation of said cap means after installation of said flexible tubing about the pressure member, said slot means terminating in an circumferentially enlarged area which is positioned in said cap means at the circumferentially outer end of said tubuing outlet slot.

4. The pressure pump of claim 1 in which said outlet slot is positioned at least 120° away from said inlet slot circumferentially about said sleeve member.

5. The pressure pump of claim 1 in which said pressure member comprises a unitary cylinder defining said generally circular periphery, and a transverse slot in said housing carries stop pin means for engaging and preventing rotation of said pressure member.

6. The pressure pump of claim 5 in which said pressure member is carried on a crank member for said orbital motion by rotation of said crank member, and electric motor means for rotating said crank member.

7. The pressure pump of claim 3 in which said pressure member is carried on a crank member for said orbital motion by rotation of said crank member, and electric motor means for rotating said crank member, said electrical motor means being controlled by multiple position switch means and circuitry adapted to provide variable resistance through said circuitry in a manner dependant upon the position of the switch of said multiple position switch means, to provde adjustable motor speed, for varying the flow rate of said pump.

8. The pressure pump of claim 7 in which diode means is provided in said circuit to prevent the electric motor means from running in reverse.

9. The pressure pump of claim 1 having tubing spirally wrapped about said pressure member more than 360°.

10. In a pressure pump for pumping fluids in flexible tubing which comprises a pressure member of generally circular periphery, adapted for obital motion about an axis of rotation, and a sleeve member positioned about said pressure member and defining channel means for receiving and retaining said flexible tubing in a predetermined position between said pressure member and sleeve member and surrounding said pressure member, the improvement comprising, in combination: said sleeve member being divided into a pair of substantially semi-circular jaws attached together at one end in hinged relation, to permit opening and closing of said jaws about said pressure member to facilitate installation of said tubing, said jaws defining opposed axial faces, one of said faces defining a tubing inlet slot transversely thereacross and the other of said opposed axial faces defining a tubing outlet slot positioned transversely thereacross each slot being of a depth corresponding to only a portion of the height of said jaws and said slots being circumferentially spaced from each other about said jaws by at least 30°, said pressure member and sleeve member being carried in a housing, said housing being carried by an openeable casing adapted to receive a flexible liquid container having flexible tubing for connection through said pressure pump, the pressure member and jaws projecting from said casing toward the exterior, said tubing inlet slot being positioned on the side of said jaws that faces said casing, at least a portion of said jaws adjacent the tubing inlet slot defining a bevelled inner edge adjacent said inlet slot and extending from said inlet slot toward the free end of said jaw, to prevent pinching and damage of the flexible tubing upon closing of the jaws.

11. The pressure pump of claim 10 in which said pressure member comprises a unitary cylinder defining said generally circular periphery, and a transverse slot in said housing carries stop pin means for engaging and preventing rotation of said pressure member.

12. The pressure pump of claim 10 in which said pressure member is carried on a crank member for said orbital motion by rotation of said crank member, and electric motor means for rotating said crank member.

13. The pressure pump of claim 10 in which said jaws are retained in removable outer cap means.

14. The pressure pump of claim 13 in which said outer cap means defines a side wall, and slot means in said side wall to permit installation of said cap means after installation of said flexible tubing about the pressure member, said slot means terminating in a circumferentially enlarged area which is positioned by said cap means at the circumferentially outer end of said tubing outlet slot.

15. In a pressure pump for pumping fluids through flexible tubing which comprises a single, integral pressure member of generally circular periphery, adapted for orbital motion about an axis of rotation and including stop means preventing rotation of the pressure member about its own axis while it moves in said orbital motion, a sleeve member positioned about said pressure member and defining channel means for receiving and retaining the flexible tubing in a predetermined position between said pressure member and sleeve member with the tubing surrounding said pressure member, said sleeve member being divided into a pair of substantially semi-circular jaws attached together at one end in hinged relation to permit opening and closing of said jaws about said pressure member to facilitate installation of said tubing, said jaws defining opposed, axial faces, one of said faces defining a tubing inlet slot positioned thereacross, and the other of the opposed axial faces defining a tubing outlet slot positioned thereacross, said slots being circumferentially spaced from each other about said jaws by at least 30°, said pressure member and sleeve member being carried by a housing, said housing being carried by an openeable casing adapted to receive a flexible liquid container having flexible tubing for connection through said pressure pump, the pressure member and jaws projecting from said casing toward the exterior, a longitudinal groove defined in said housing to receive said flexible tubing, said tubing inlet slot being positioned on the side of said jaws that face said casing, an end of said tubing inlet slot being positioned adjacent to the outer end of said longitudinal groove, to permit tubing in said longitudinal groove to pass into said inlet slot.

16. The pressure pump of claim 15 in which said pressure member is carried on a crank member for said orbital motion by rotation of said crank member, and electric motor means for rotating said crank member.

17. In a pressure pump for pumping fluids through flexible tubing which comprises a pressure member of generally circular periphery adapted for orbital motion about an axis of rotation, and a sleeve member positioned about said pressure member and defining channel means for receiving and retaining said flexible tubing in a predetermined position between said pressure member and sleeve member with the tubing surrounding said pressure member, the improvement comprising, in combination:

said sleeve member being divided into a pair of substantially semi-circular jaws attached together at one end in hinged relation, to permit opening and closing of said jaws about said pressure member to facilitate installation of said tubing, said pressure member and sleeve member being carried by a housing, said housing being carried by an openable casing adapted to receive a flexible liquid container having flexible tubing for connection through said pressure pump, the pressure member and jaws projecting from said casing toward the exterior, a longitudinal groove defined in said housing to receive said flexible tubing, and a tubing inlet slot positioned on the side of said jaws that faces said casing, an end of said tubing inlet slot being positioned adjacent to the outer end of said longitudinal groove, to permit tubing in said longitudinal groove to pass into said inlet slot.

18. The pressure pump of claim 17 having tubing spirally wrapped about said pressure member more than 360°.

19. In a pressure pump for pumping fluids in flexible tubing which comprises a pressure member of generally circular periphery, adapted for orbital motion about an axis of rotation, and a sleeve member positioned about said pressure member and defining channel means for receiving and retaining said flexible tubing in a predetermined position between said pressure member and sleeve member and surrounding said pressure member, the improvement comprising, in combination:

said sleeve member being divided into a pair of substantially semi-circular jaws attached together at one end in hinged relation, to permit opening and closing of said jaws about said pressure member to facilitate installation of said tubing, said jaws defining a tubing inlet slot transversely across one side of one of said jaws, and a tubing outlet slot positioned transversely across the opposite side of the other of said jaws, each slot being of a depth corresponding to only a portion of the height of said jaws and said slots being circumferentially spaced from each other about said jaws by at least 30°, said pressure member and sleeve member being carried in a housing, said housing being carried by an openable casing adapted to receive a flexible liquid container having flexible tubing for connection through said pressure pump, the pressure member and jaws projecting from said casing toward the exterior, said tubing inlet slot being positioned on the side of said jaws that faces said casing, a longitudinal groove defined in said housing to receive said flexible tubing, an end of said tubing inlet slot being positioned adjacent to the outer end of said longitudinal groove to permit tubing in said longitudinal groove to pass into said inlet slot, to wind in spiral manner more than 360° about said orbital member, and to exit from the tubing outlet slot.

20. The pressure pump of claim 19 in which stop means are provided preventing rotation of the pressure member about its own axis while it moves in said orbital motion.

* * * * *